United States Patent
Carbunaru et al.

(10) Patent No.: US 8,313,453 B2
(45) Date of Patent: Nov. 20, 2012

(54) BURR HOLE SEALING DEVICE FOR PREVENTING BRAIN SHIFT

(75) Inventors: Rafael Carbunaru, Valley Village, CA (US); Todd K. Whitehurst, Valencia, CA (US); Andrew DiGiore, Santa Monica, CA (US); Kristen Jaax, Santa Clara, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 490 days.

(21) Appl. No.: 12/549,174

(22) Filed: Aug. 27, 2009

(65) Prior Publication Data

US 2011/0054518 A1   Mar. 3, 2011

(51) Int. Cl.
*A61M 5/00* (2006.01)
(52) U.S. Cl. ............................................. 604/8
(58) Field of Classification Search .................. 604/8, 9; 606/129, 130, 213; 607/45, 116
See application file for complete search history.

(56) References Cited

U.S. PATENT DOCUMENTS

| | | | | |
|---|---|---|---|---|
| 4,114,603 | A * | 9/1978 | Wilkinson | 600/561 |
| 5,464,446 | A * | 11/1995 | Dreessen et al. | 607/116 |
| 5,732,699 | A | 3/1998 | Lundback | |
| 5,891,028 | A | 4/1999 | Lundback | |
| 5,927,277 | A | 7/1999 | Baudino et al. | |
| 5,954,687 | A * | 9/1999 | Baudino | 604/48 |
| 6,845,267 | B2 | 1/2005 | Harrison et al. | |
| 6,920,359 | B2 | 7/2005 | Meadows et al. | |
| 6,950,707 | B2 | 9/2005 | Whitehurst | |
| 7,004,948 | B1 | 2/2006 | Pianca et al. | |
| 7,343,205 | B1 | 3/2008 | Pianca et al. | |
| 7,369,899 | B2 | 5/2008 | Malinowski et al. | |
| 7,479,146 | B2 | 1/2009 | Malinowski et al. | |

(Continued)

FOREIGN PATENT DOCUMENTS

WO   WO2009055746 A2   4/2009

OTHER PUBLICATIONS

Roberts DW, Hartov A. Kennedy FE, Miga MI, Paulsen KD: Intraoperative brain shift and deformation: A quantitative analysis of cortical displacement in 28 cases. Neurosurgery 43:749-760, 1998.
Dickhaus H., Ganser KA, Stuabert A., Bonsanto MM, Wirtz CR, Tronnier VM, Kunze S: Quantification of brain shift effects by MR-imaging. Engineering in Medicine and Biology Society vol. 2: 491-494, 1997.

(Continued)

*Primary Examiner* — Nicholas Lucchesi
*Assistant Examiner* — Aarti B Berdichevsky
(74) *Attorney, Agent, or Firm* — Vista IP Law Group LLP (57) ABSTRACT

A burr hole sealing device for preventing brain shift during a stimulation lead implantation procedure is provided. The device includes a suction cup ring and a self-sealing membrane positioned within the aperture of the ring. The sealing device is attached adjacent to a burr hole and over a dura layer that is exposed in the bottom of the burr hole. The stimulation lead is disposed through the burr hole, through the membrane, through the dura layer and into brain tissue. The membrane is configured to allow the lead to pass therethrough while maintaining a tight seal around the diameter of the lead, thereby hindering leakage of cerebrospinal fluid out of the cranial cavity and maintaining a substantially fixed intracranial pressure. In one embodiment, the sealing device includes a syringe for adding fluid to, or removing fluid from, the cranial cavity in response to a detected change in intracranial pressure.

11 Claims, 9 Drawing Sheets

U.S. PATENT DOCUMENTS

| | | |
|---|---|---|
| 2002/0052610 A1* | 5/2002 | Skakoon et al. ............ 606/129 |
| 2004/0034367 A1 | 2/2004 | Malinowski |
| 2005/0070458 A1* | 3/2005 | John .............................. 514/1 |
| 2006/0190054 A1 | 8/2006 | Malinowski et al. |
| 2006/0190055 A1 | 8/2006 | Malinowski et al. |
| 2007/0233158 A1 | 10/2007 | Rodriguez |
| 2008/0243219 A1 | 10/2008 | Malinowski et al. |
| 2009/0112327 A1 | 4/2009 | Lane et al. |
| 2009/0118804 A1 | 5/2009 | Moffitt et al. |
| 2009/0182351 A1 | 7/2009 | Malinowski |
| 2010/0023020 A1* | 1/2010 | Barker .......................... 606/129 |
| 2010/0023100 A1* | 1/2010 | Barker .......................... 607/116 |

OTHER PUBLICATIONS

Nimsky C., Gansland O., Cemy S., Hastreiter P, Greiner G., Fahlbusch R.: Quantification of, visualization of, and compensation for brain shift using intraoperative magnetic resonance imaging. Neurosurgery 47, 1070-1080, 2000.

Winkler D., Tittgemeyer M., Schwartz J., Preul C., Strecker K., Meixensberger J.: The first evaluation of brain shift during functional neurosurgery by deformation field analysis. Journal of Neurology, Neurosurgery, and Psychiatry 76 (8): 1161-3, 2005.

* cited by examiner

BURR HOLE SEALING DEVICE FOR PREVENTING BRAIN SHIFT

FIELD OF THE INVENTION

The present inventions relate to apparatus and methods for preventing brain shift during the insertion of elongated medical devices, such as catheters or leads, through a cranial burr hole.

BACKGROUND OF THE INVENTION

Deep brain stimulation (DBS) and other related procedures involving implantation of electrical stimulation leads within the brain of a patient are increasingly used to treat disorders, such as Parkinson's disease, dystonia, essential tremor, seizure disorders, obesity, depression, restoration of motor control, and other debilitating diseases via electrical stimulation of one or more target sites, including the ventrolateral thalamus, internal segment of globus pallidus, substantia nigra pars reticulate, subthalamic nucleus, or external segment of globus pallidus. DBS has become a prominent treatment option for many disorders, because it is a safe, reversible alternative to lesioning. For example, DBS is the most frequently performed surgical disorder for the treatment of advanced Parkinson's Disease. There have been approximately 30,000 patients world-wide that have undergone DBS surgery. Consequently, there is a large population of patients who will benefit from advances in DBS treatment options.

During DBS procedures, at least one burr hole is meticulously cut through the patient's cranium without puncturing the dura layer that lines the inner surface of the skull or damaging the brain tissue below. A large stereotactic targeting apparatus is then mounted to the patient's cranium, and a cannula is scrupulously positioned towards the target site in the brain. A stimulation lead is then introduced through the cannula, through the burr hole, through the exposed dura layer, and into the parenchyma of the brain, such that one or more electrodes located on the lead are strategically placed at a target site in the brain of the patient. Typically, an imaging device, such as a magnetic resonant imager (MRI), will be used to visualize the lead relative to the target site. Once the lead is properly positioned, the portion of the lead exiting the burr hole is subcutaneously routed underneath the patient's scalp to an implantable pulse generator (IPG) implanted in the patient at a site remote from the burr hole (e.g., the patient's shoulder or chest region). Further details discussing the treatment of diseases using DBS are disclosed in U.S. Pat. Nos. 6,845,267 and 6,950,707, both of which are expressly incorporated herein by reference.

Significantly, it is crucial that proper location and maintenance of the lead position be accomplished in order to continuously achieve efficacious therapy. This is especially so with DBS applications, in which cases, the target site (or sites) that is intended for electrical stimulation is about the size of a pea and is located deep within the patient's brain. Thus, lead displacements of less than a millimeter may have a deleterious effect on the patient's therapy. Therefore, it is important that the electrode(s) of the lead be accurately located at the target site and that such electrode(s) be securely maintained at the target site during and after implantation of the lead.

Brain shift is a prevalent source of significant error in the implantation of stimulation leads. Brain shift may include the movement and deformation of the brain during an operation. For example, when the dura is punctured to access brain tissue during the stimulation lead implantation procedure described above, sub-cranial contents may shift significantly due to cerebrospinal fluid (CSF) leaking out of the burr hole, which causes a change in intracranial pressure. Surgeons rely on pre-operation MRI scans to pinpoint the electrodes' targets and these targets must be hit with millimeter-quality accuracy. Fixed fiducials on the surface of the cranium are used as reference points for the insertions. However, these fiducials cannot take into account the shifting of the sub-cranial contents, and by the time the actual leads are implanted, the MRI guiding the physicians is inaccurate. Over the course of a surgery, comprehensive studies have often recorded average brain displacements approaching or exceeding ten millimeters, which is an unacceptable margin of error. The result is that doctors are forced to use blind guess-and-check methods in order to locate points deep within the brain.

Brain shift is generally caused by settling of the brain, often facilitated by a leakage of CSF and the resulting decrease of intracranial pressure and buoyancy. This could be caused by a failure to seal a burr hole when dura puncture occurs, another such related accident, or may be an innate aspect of some surgical techniques. Brain shift is not always uniform deep within the tissue, adding the complication of deformation. The primary force driving brain shift is invariably gravity, though deformation could potentially be caused by osmotic drugs that change the brain's water concentrations. A study of pre-operation MRIs has shown that brain shift from changes in patient position is insignificant (less than 1 mm).

To address these issues, there are several protocols now being developed to compensate for the discrepancy between the MRI and the shifted brain. The most effective of these involve intra-operative MRIs, ultrasounds, or optical scanners designed to update the MRI over the course of the surgery. MRIs, in particular, provide the most information, but are prohibitively expensive, with unit prices in the millions of dollars, and take far too long per scan to be efficient in the operating room. In addition, not all components of current DBS systems (e.g., the leads) are MRI compatible. Thus, the use of MRI during surgery may not be advantageous. Other methods involve the creation of computer models to predict displacement.

As an alternative to compensating for brain shift, there remains a need for reducing or preventing brain shift in a manner that is medically and financially preferable.

SUMMARY OF THE INVENTION

In accordance with a first aspect of the present inventions, a burr hole sealing apparatus is provided. The apparatus includes a suction cup ring configured for forming a vacuum seal with tissue adjacent to a cranial burr hole, the suction cup ring having an inner diameter, an outer diameter, a central opening, a convex upper surface between the inner and outer diameters, and a concave lower surface between the inner and outer diameters. In one embodiment, the ring is configured for being positioned within the cranial burr hole and for being attached directly to a dura layer that is exposed at a bottom of the burr hole. Thus, the outer diameter of the ring may be less than or equal to a diameter of the burr hole. In another embodiment, the suction cup ring may be configured for forming a vacuum seal with a skull bone that surrounds a top of the burr hole. Thus, the inner diameter of the ring may be greater than a diameter of the burr hole.

The apparatus also includes an inner membrane of puncturable, self-sealing material disposed within the central opening. The inner membrane may be configured for being punctured by an elongated medical device and for allowing the medical device to pass therethrough while maintaining a tight seal around a diameter of the medical device. The inner membrane may be attached directly to the inner diameter of the ring. Alternatively, the inner membrane may be configured for being disposed within the central opening by removably attaching to an attachment portion of the apparatus. The attachment portion may be a threaded collar disposed within the central opening of the ring. The apparatus may further include a tab configured for releasing the vacuum seal.

The burr hole sealing apparatus may further include a syringe for adding fluid to and removing fluid from a cranial cavity through the cranial burr hole. In one embodiment, the syringe includes a central passageway and a fluid chamber surrounding the central passageway, wherein the central passageway is configured for allowing an elongated medical device to pass therethrough. The inner membrane may be disposed on a distal end of the central passageway, and a fluid opening may be disposed on a distal end of the fluid chamber, such that the fluid opening may at least partially surround the inner membrane. In another embodiment, the syringe may include a needle configured for puncturing a dura layer and allowing fluid to flow between the fluid chamber and the cranial cavity. The needle may be configured for puncturing the inner membrane.

The syringe of the burr hole sealing apparatus may include a manually operated plunger. Alternatively, the apparatus may have a pressure transducer for monitoring a pressure within the cranial cavity, such that the apparatus may be configured for automatically maintaining the pressure at a substantially fixed pressure level by maintaining a volume of cerebrospinal fluid within the cranial cavity at a substantially fixed fluid level. A pressure regulator may be in communication with the pressure transducer, and the syringe may include an automatically operated plunger configured for being operated by the pressure regulator.

In accordance with a second aspect of the present inventions, a method for performing a medical procedure on a patient is provided. The method includes attaching a burr hole sealing device adjacent to a cranial burr hole that exposes a dura layer, wherein the burr hole sealing device includes an aperture disposed over the exposed dura layer. The burr hole sealing device may include a syringe and an inner membrane disposed within the aperture. The method may further comprise puncturing the inner membrane with the syringe. In one embodiment, the burr hole sealing device has a suction cup ring. The burr hole sealing device may be attached adjacent to the burr hole by vacuum sealing the suction cup ring to a surface adjacent to the burr hole and attaching the inner membrane to the ring. The surface adjacent to the burr hole may be a top surface of a skull bone that surrounds the burr hole. Alternatively, the surface adjacent to the burr hole may be the dura layer.

The method also includes introducing an elongated medical device through the aperture of the sealing device, through the burr hole, through the dura layer, and into the brain tissue of the patient. The syringe may have a central channel and the elongated medical device may be introduced by passing the elongated medical device through the central channel in the syringe. Introducing the elongated medical device through the aperture of the sealing device may also include introducing the elongated medical device through the inner membrane.

The method further includes allowing the sealing device to maintain a substantially fixed intracranial pressure while the medical device is disposed through the dura layer. Maintaining the substantially fixed intracranial pressure may include maintaining a substantially fixed volume of cerebrospinal fluid within a cranial cavity. The substantially fixed intracranial pressure may be maintained actively or passively. Actively maintaining the substantially fixed intracranial pressure may include automatically or manually operating the sealing device.

In one embodiment, maintaining the substantially fixed intracranial pressure includes monitoring the intracranial pressure, adding fluid into a cranial cavity if a decrease in the intracranial pressure is detected, and removing fluid from the cranial cavity if an increase in the intracranial pressure is detected. Adding and removing the fluid may be done by using the syringe. Further, the syringe may include a fluid chamber surrounding the central channel, and adding and removing the fluid may be performed through the fluid chamber.

In accordance with a third aspect of the present inventions, a burr hole sealing system is provided. The burr hole sealing system includes a sealing mechanism configured to be attached adjacent a cranial burr hole, to allow an elongated medical device to be disposed through a dura layer and into a cranial cavity, and to hinder leakage of cerebrospinal fluid from the cranial cavity while the elongated medical device is disposed through the dura layer. The sealing mechanism may be configured for adhering to tissue adjacent to the burr hole. In addition, the sealing mechanism may be configured for forming a seal around a diameter of the elongated medical device while the elongated medical device is disposed through the dura layer. The sealing mechanism may include an inner membrane configured for forming a seal around a diameter of the elongated medical device while the elongated medical device is disposed through the dura layer. The sealing device may also include a suction cup ring having an aperture, and the inner membrane may be disposed within the aperture of the suction cup ring.

The burr hole sealing system also includes a syringe attached to the sealing mechanism and configured for maintaining a substantially fixed intracranial pressure within the cranial cavity while the elongated medical device is disposed through the dura layer. The syringe may comprise a central passage, a fluid chamber surrounding the central passage, and a membrane on a distal end of the central passage. The central passage and the membrane may be configured for allowing the elongated medical device to pass therethrough. The syringe may also include a plunger. The plunger may be manually operated or automatically operated.

The burr hole sealing system may further include a pressure transducer configured for monitoring the intracranial pressure. In addition, the system may have a pressure regulator in communication with the pressure transducer, wherein the pressure regulator may be configured for automatically operating the plunger in response to a change in pressure detected by the pressure transducer.

In accordance with a fourth aspect of the present inventions, a kit for preventing brain shift is provided. The kit includes an attachment mechanism configured for adhering to tissue adjacent to a cranial burr hole and for allowing an elongated medical device to be disposed through a dura layer and into a cranial cavity. The attachment mechanism may comprise an aperture therethrough, and the kit may further comprise a membrane configured for being disposed within the aperture and for forming a seal around the elongated medical device while the elongated medical device is disposed through the dura layer. The attachment mechanism may have a suction cup ring and the membrane may be attached directly to the suction cup ring. The attachment mechanism may be configured for adhering to the dura layer or for adhering to a skull bone that surrounds a top of the burr hole.

The kit also includes a syringe configured for engaging the attachment mechanism and for maintaining a substantially fixed intracranial pressure within the cranial cavity while the elongated medical device is disposed through the dura layer. The syringe may be configured for puncturing and passing through the membrane disposed within the aperture of the attachment mechanism. The membrane may be attached directly to a distal end of the syringe. The syringe may be configured for attaching to the attachment mechanism via cooperating threads on the attachment mechanism and the distal end of the syringe. The syringe may have a central passageway configured for allowing the elongated medical device to pass therethrough, and a fluid chamber at least partially surrounding the central passageway. A manually operated plunger may be coupled to the fluid chamber.

The kit may also include a pressure transducer configured for monitoring the intracranial pressure. In addition, the kit may comprise a pressure regulator configured for being coupled to the pressure transducer and for automatically operating the syringe.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Figure 1:
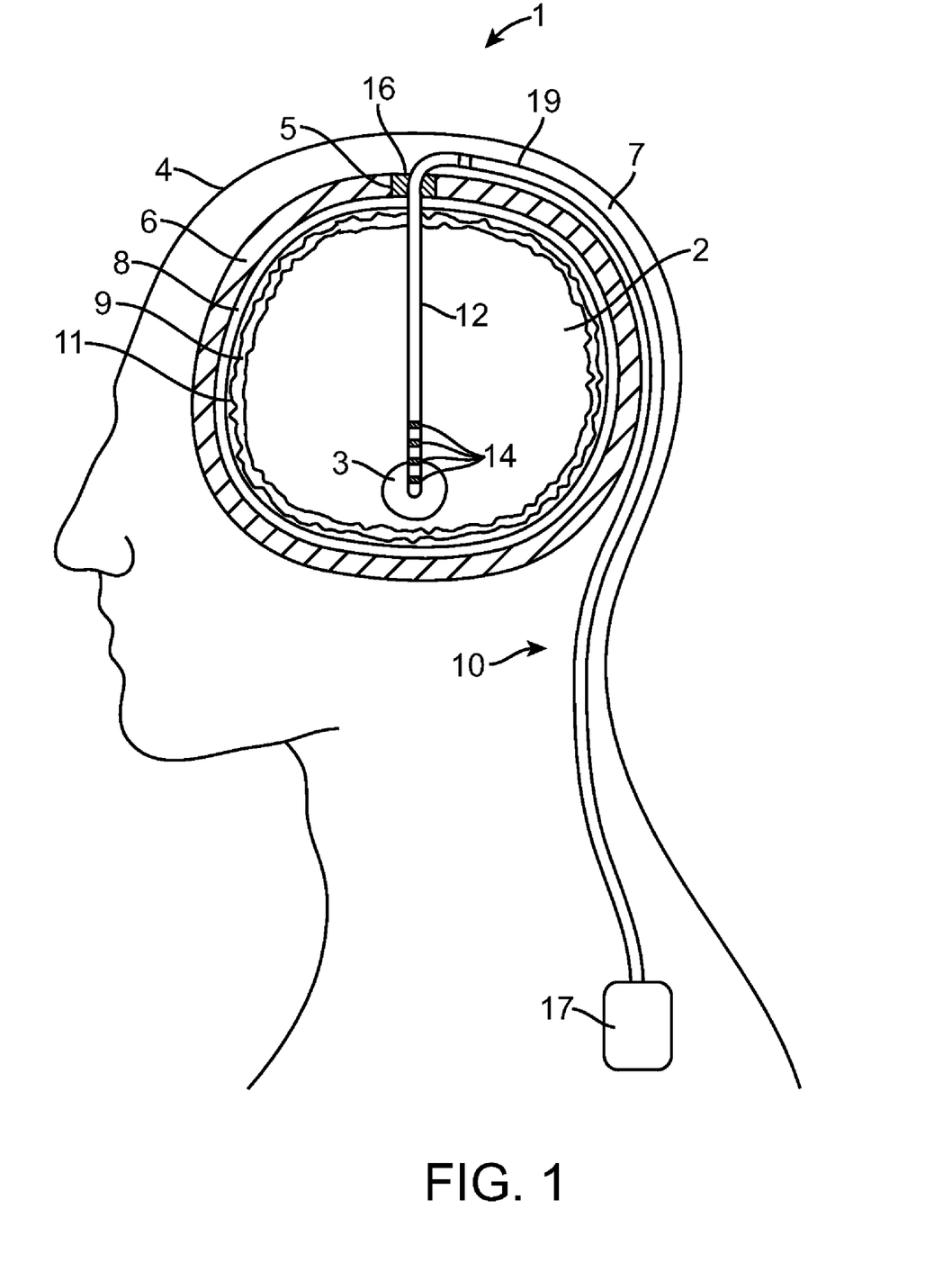
FIG. 1 is a plan view of a Deep Brain Stimulation (DBS) system implanted within a patient.

Turning first to FIG. 1, an exemplary DBS system 10 constructed in accordance with one embodiment of the present inventions is shown implanted within a patient 1 for the treatment of a debilitating disease such as, Parkinson's disease, dystonia, essential tremor, seizure disorders, obesity, depression, etc. The system 10 comprises a stimulation lead 12 implanted within the parenchyma of the brain 2 in order to position electrodes 14 carried by the distal end of the stimulation lead 12 adjacent a target tissue region 3, such as a deep brain structure of the patient 1 (e.g., the ventrolateral thalamus, internal segment of globus pallidus, substantia nigra pars reticulate, subthalamic nucleus, or external segment of globus pallidus). Thus, electrical stimulation energy can be conveyed from the electrodes 14 to the target tissue region 3 to treat the disease. As can be seen, the stimulation lead 12 is introduced into the head 4 of the patient 1 via a burr hole 5 formed in the cranium 6 of the patient 1. In alternative embodiments, multiple stimulation leads (not shown) may be used, all of which may be located within the head 4 of the patient 1 via the same burr hole 5.

To secure the stimulation lead 12 (or leads), the system 10 further comprises a burr hole plug 16 mounted to the cranium 6 around the burr hole 5 of the patient 1. The stimulation lead 12 extends from the burr hole 5, through the burr hole plug 16, to a location external to the cranium 6. The DBS system 10 further comprises a neurostimulator 17, such as an implantable pulse generator (IPG), radio frequency (RF) receiver-stimulator, or any other device coupled to and capable of delivering electrical stimulation energy to the stimulation lead 12 in a controlled and therapeutic manner. The neurostimulator 17 may be generally implanted in a surgically-made pocket in the torso of the patient (e.g., the chest or shoulder region). The neurostimulator 17 may, of course, also be implanted in other locations of the patient's body. The DBS system 10 further comprises a lead extension 19, which may be suitably connected to the proximal end of the stimulation lead 12 and subcutaneously advanced underneath the scalp 7 of the patient 1 to the neurostimulator implantation site, thereby facilitating the location of the neurostimulator 17 away from the exit point of the stimulation lead 12 (i.e., the burr hole 5). In alternative embodiments, the neurostimulator 17 may be directly implanted on or within the cranium 6 of the patient 1, as described in U.S. Pat. No. 6,920,359, which is expressly incorporated herein by reference. In this case, the lead extension 19 may not be needed.

After implantation, the neurostimulator 17 is used to provide the therapeutic stimulation under control of the patient 1. The system 10 may include external components, such as a patient handheld programmer, a clinician programming station, and an external charger (all not shown), the details of which will not be described herein for purposes of brevity.

As described previously herein, during the implantation procedure, the stimulation lead 12 passes through the burr hole 5 and punctures the dura layer 8, which may cause CSF 11 to leak out of the cranial cavity 9, thereby causing a change in intracranial pressure, and significant brain shift. Therefore, embodiments of the present invention relate to apparatus and methods for preventing or reducing brain shift during the implantation of elongated medical devices, such as catheters or stimulation leads, through a cranial burr hole by preventing or hindering leakage of CSF. In this manner, embodiments may advantageously be installed after a burr hole 5 has been formed and may advantageously form a seal around the diameter of the stimulation lead 12 as the stimulation lead 12 is disposed through the burr hole 5, through the dura layer 8 and into the brain tissue 2, thereby hindering leakage of CSF 11 out of the cranial cavity 9. Some of the embodiments include mechanisms for actively regulating intracranial pressure, and, thus, may be installed after the dura layer 8 has been punctured.

It should be understood that, while the invention lends itself well to applications in DBS, the invention, in its broadest aspects, may not be so limited. For example, the stimulation lead 12 (or leads) can be delivered within regions of the brain other than a deep brain structure, e.g., within or on the surface of the cerebral cortex. In addition, electrical leads, other than stimulation leads, may be delivered within the head 4 of the patient 1. For example, an electrical recording lead can be delivered into the head 4 of the patient 1 via the burr hole 5 to sense brain signals, either alone or in conjunction with a stimulation lead. Further, elongated medical devices other than electrical leads, for example, drug delivery catheters or needles, may be delivered into the head 4 of the patient 1 via the burr hole 5. Thus, it can be appreciated that the burr hole sealing apparatus described herein can be used with any elongated medical device intended to be delivered through a burr hole 5 within the cranium 6 of a patient 1 for any therapeutic and/or diagnostic purpose.

Figure 2A:
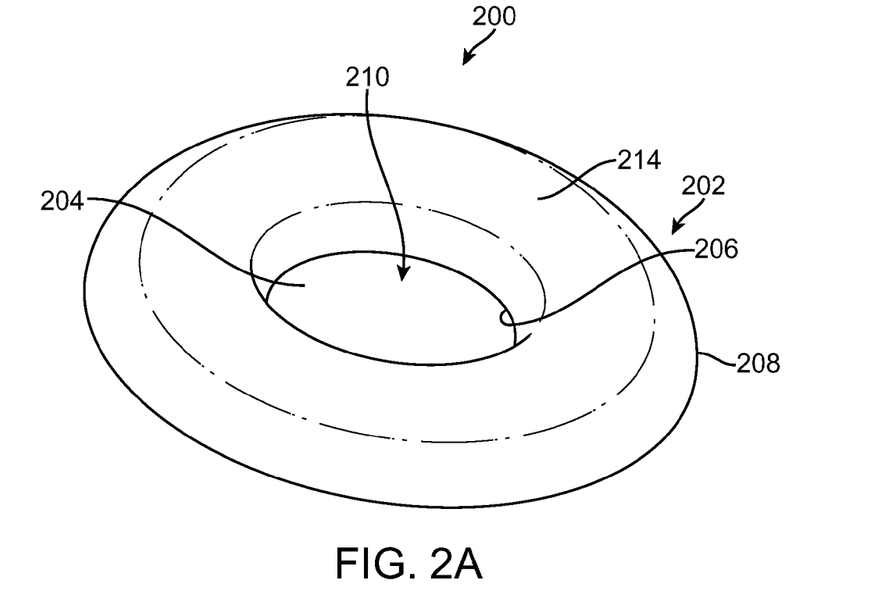
FIG. 2A is a perspective view of a burr hole sealing device constructed in accordance with one embodiment of the present inventions.
Figure 2B:
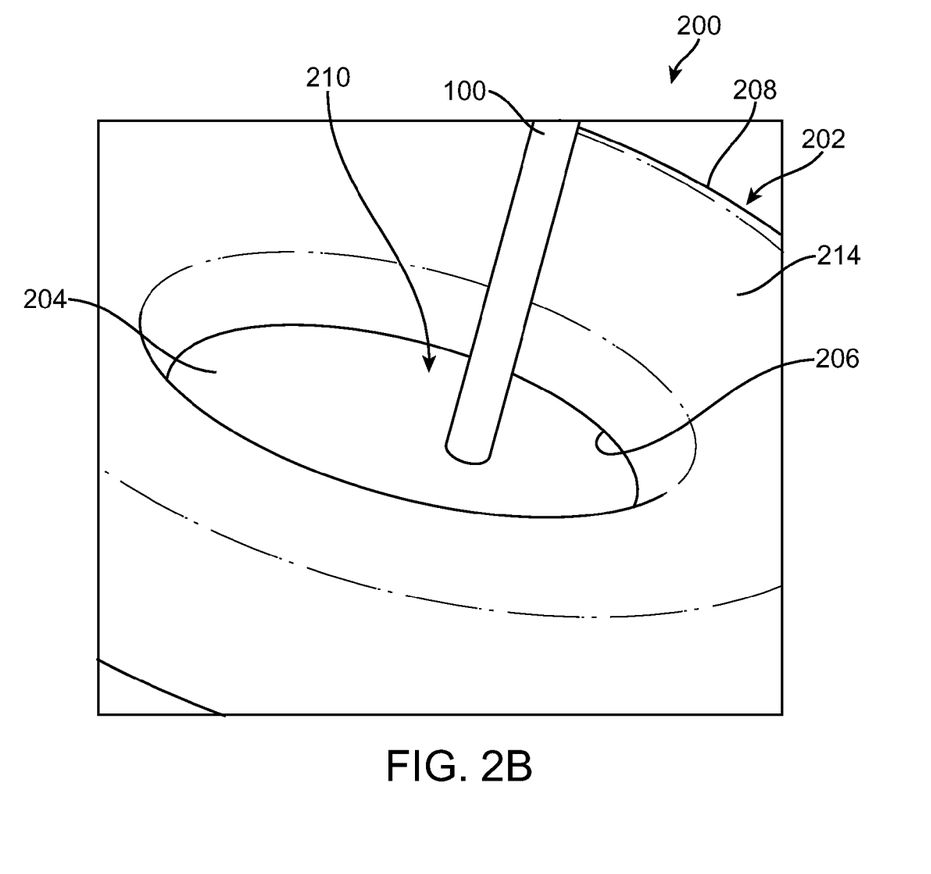
FIG. 2B is a perspective view of an elongated medical device passing through the burr hole sealing device depicted in FIG. 2A.

Referring now to FIGS. 2A-2B, one embodiment of a burr hole sealing device 200 will be described. The burr hole sealing device 200 generally includes an attachment mechanism, such as a suction cup ring 202, and an inner membrane 204. The suction cup ring 202 has an inner diameter 206, an outer diameter 208, an aperture 210, a concave lower surface 212 (shown in FIG. 3A) and a convex upper surface 214, and is configured for forming a vacuum seal with tissue adjacent to a burr hole, as discussed in more detail below.

Although the suction cup ring 202 is depicted as being circular in nature, the ring 202 may alternatively be of a different shape, such as oval, square, hexagonal, etc. Furthermore, although the use of a suction cup ring provides a very efficient and effective means for forming a vacuum seal, other attachment mechanisms may be used. For example, rather than a suction cup, a flat ring having an adhesive lower surface may surround the membrane 204. In another alternative, the membrane 204 itself may have an adhesive lower surface such that the membrane 204 may adhere directly onto the dura layer 8.

The inner membrane 204 is formed of a self-sealing material, e.g., rubber or the like, that is configured for being punctured by the stimulation lead 100 and for forming a tight seal around the lead 100 as the lead 100 passes through the membrane 204, as shown in more detail in FIG. 2B. In this embodiment, the inner membrane 204 is attached directly to the inner diameter 206 of the ring 202.

Figure 3A:
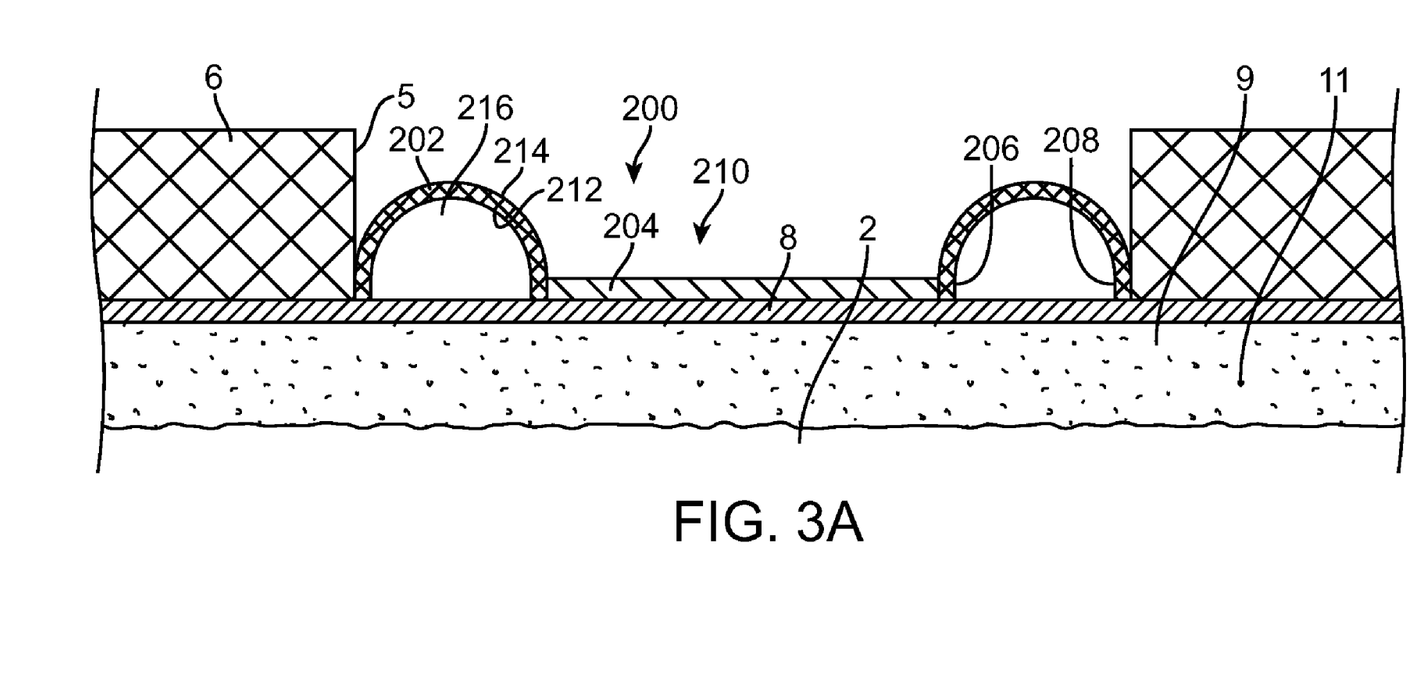
FIG. 3A is a cross-sectional view taken along line 3A-3A in FIG. 2A of the burr hole sealing device depicted in FIGS. 2A-2B disposed within a cranial burr hole, in accordance with one embodiment of the present inventions.

During use, the sealing device 200 may be positioned within the burr hole 5, and preferably attaches to the dura layer 8 that is exposed at the bottom of the burr hole 5, as shown in FIG. 3A. Thus, the size of the device 200 matches the size of the burr hole 5. In this case, the outer diameter 208 of the suction cup ring 202 is less than or equal to the diameter of the burr hole 5. With this arrangement, leakage of CSF 11 into the space between the dura layer 8 and the cranium 6 is substantially prevented.

Figure 4:
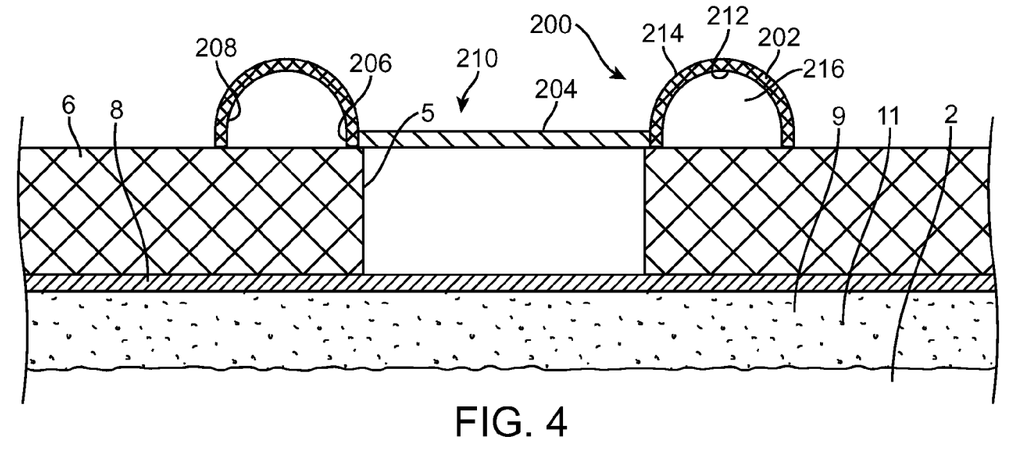
FIG. 4 is a cross-sectional view taken along line 3A-3A of the burr hole sealing device depicted in FIGS. 2A-2B disposed above a cranial burr hole, in accordance with another embodiment of the present inventions.

The device 200 may alternatively be adhered to the portion of the skull 6 that surrounds the top of the burr hole 5, as shown in FIG. 4. In this embodiment, the diameter of the inner membrane 204 is greater than or equal to the diameter of the burr hole 5 so that the membrane 204 bridges the burr hole 5. It should be well understood that, in this embodiment, the size of the sealing device 200 does not necessarily match the size of the burr hole 5, so long as the inner membrane 204 completely seals the burr hole 5. For example, rather than having a ring shape, the attachment mechanism 202 could alternatively be ovular, square, hexagonal, etc., so long as the aperture in the attachment mechanism is larger than the burr hole 5 so that the inner membrane 204 bridges the burr hole 5.

The suction cup ring 202 may be made of material (e.g., silicone) that is sufficiently flexible to allow for deformation of the suction cup ring 202 in order to engage the vacuum seal between the ring 202 and the tissue surface (e.g., the skull bone 6 or the dura layer 8, as discussed above). That is, the sealing device 200 is adhered to tissue adjacent to the burr hole 5 by pressing the suction cup ring 202 onto the surface of the tissue, thereby allowing air to escape from the cavity 216 between the suction cup ring 202 and the surface of the tissue and reducing the air pressure within the cavity 216. Thus, the suction cup ring 202 attaches to the surface of the tissue by suction force. Alternatively, the suction cup ring 202 may include a one-way valve for removing air from the cavity 216, a needle for applying negative pressure, or other such mechanism for removing air from the cavity 216 to form the vacuum seal. Additionally or alternatively, a layer of sealing gel, grease or oil may be applied between the suction cup ring 202 and the surface in order to facilitate the suction between the suction cup ring 202 and the surface.

Figure 3B:
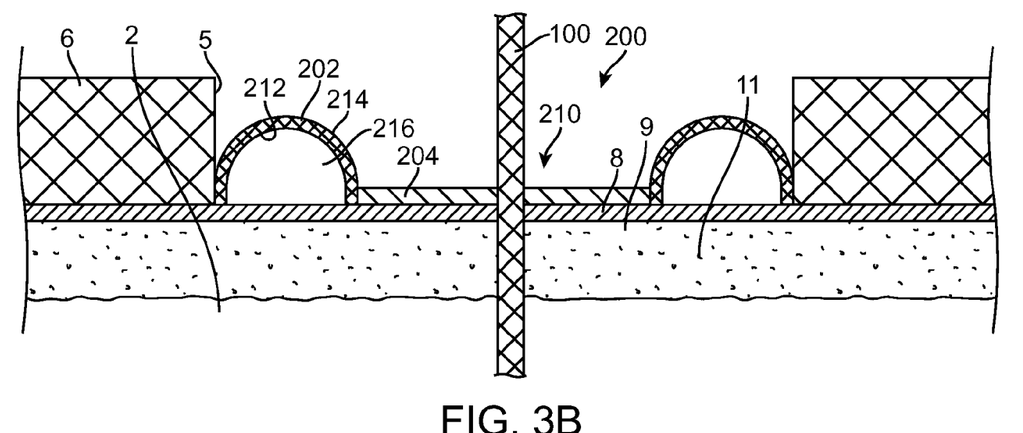
FIG. 3B is a cross-sectional view taken along line 3B-3B in FIG. 2B of the burr hole sealing device depicted in FIGS. 2A-2B disposed within a cranial burr hole with an elongated medical device disposed therethrough.

After attaching the sealing device 200 to the tissue surface, as shown in FIGS. 3A and 4, the stimulation lead 100 is disposed through the burr hole 5, through the aperture 210 of the ring 202, through the membrane 204, through the dura layer 8 and into the brain tissue 2, as shown in FIG. 3B. Thus, the burr hole sealing device 200 is a single-piece, passive device for reducing, preventing, or hindering leakage of CSF 11 out of the cranial cavity 9 during implantation of the stimulation lead 100. By hindering leakage and therefore maintaining a substantially constant volume of fluid within the cranial cavity 9, the intracranial pressure change that is the primary cause of brain shift is substantially eliminated.

Referring now to FIGS. 5A-5E, another embodiment of a burr hole sealing device 500 will be described. In this embodiment, the burr hole sealing device 500 includes a syringe 520 for actively maintaining a substantially fixed intracranial pressure. The device 500 also includes an attachment mechanism, or suction cup ring 502, for adhering to tissue adjacent to a burr hole in a manner substantially similar to the suction cup ring 202 shown in FIGS. 2A-4. The syringe 520 attaches to the suction cup ring 502 via an attachment portion, which, in this embodiment, comprises a threaded collar 527, and cooperating threads 522 and 524 disposed on the collar 527 and on the distal end of the syringe 520, respectively. However, it should be well understood that the attachment portion may alternatively comprise adhesive, a friction fit engagement, or the like.

Figure 5A:
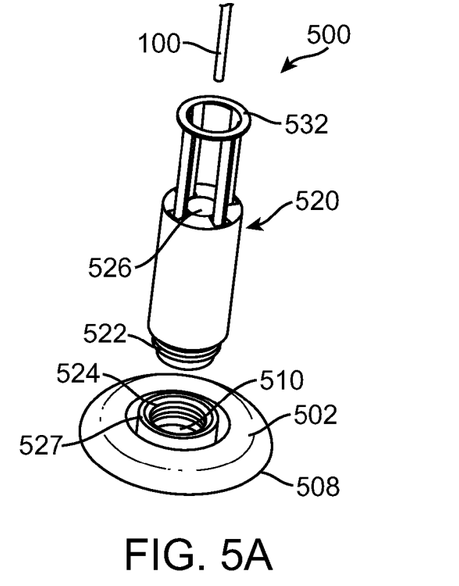
FIGS. 5A and 5B are partially exploded perspective views of a burr hole sealing device constructed in accordance with another embodiment of the present inventions.
Figure 5B:
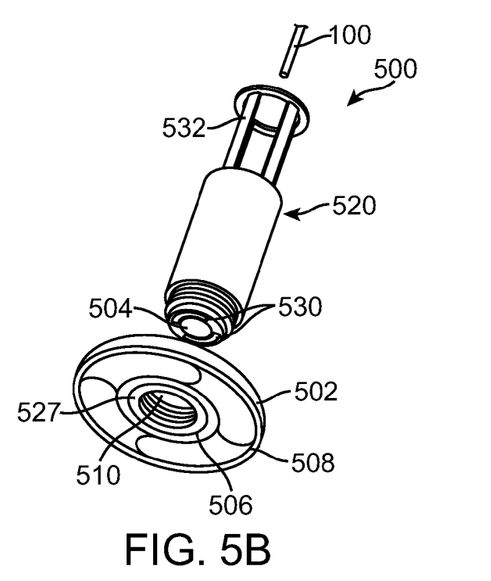
Figure 5C:
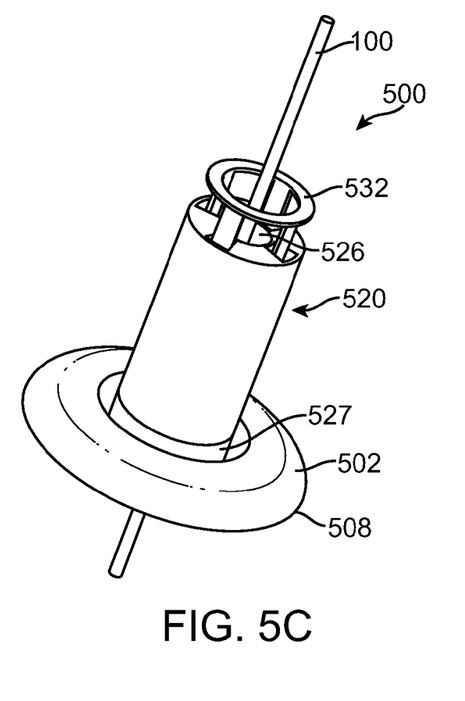
FIGS. 5C and 5D are perspective views of the burr hole sealing device depicted in FIGS. 5A and 5B.
Figure 5D:
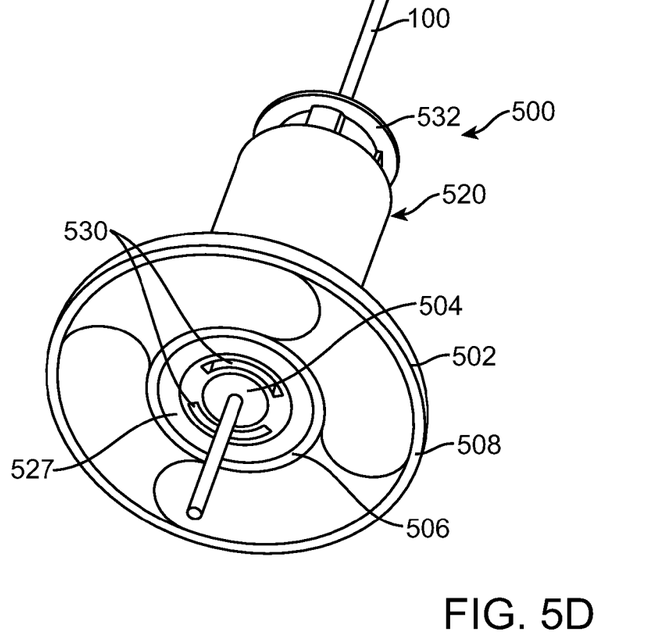
Figure 5E:
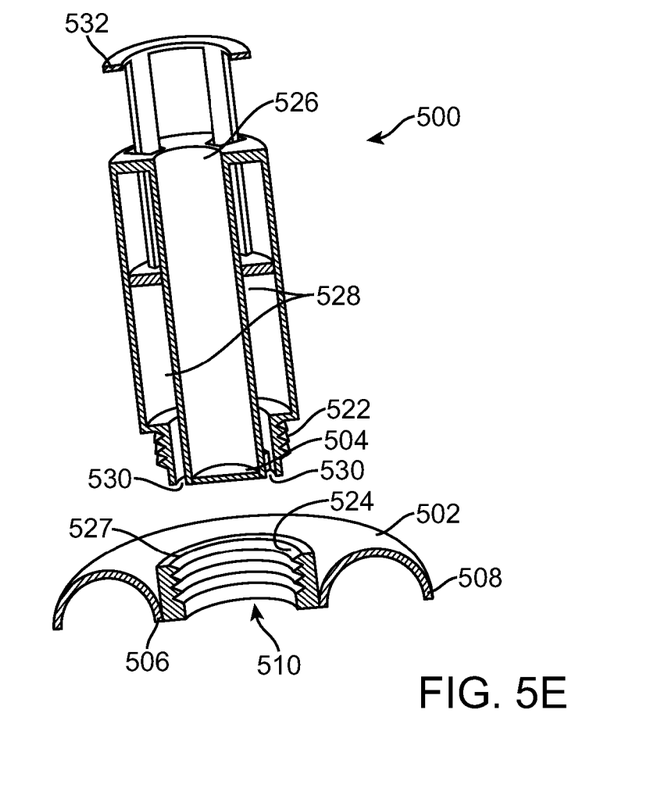
FIG. 5E is a cross-sectional view of the burr hole sealing device depicted in FIGS. 5A-5D.

As shown in FIG. 5E, the syringe 520 has a central channel 526 and a fluid chamber 528 surrounding the central channel 526. An inner membrane 504 is disposed on the distal end of the central channel 526. In this manner, the inner membrane 504 is disposed within the aperture 510 of the ring 502 when the syringe 520 is attached to the ring 502, as shown in FIG. 5D. The distal end of the fluid chamber 528 terminates in a fluid opening 530 that at least partially surrounds the inner membrane 504. The syringe 520 also includes a manually operated plunger 532.

The sealing device 500 may also include a pressure transducer (not shown) for monitoring the intracranial pressure. The pressure transducer may include sensors that are capacitance, resistance or induction-based. In addition, the pressure transducer may be ASIC-based, MEMS-based, or the like.

The desired intracranial pressure which the sealing device 500 is configured to maintain is preferably equal to the intracranial pressure that exists prior to puncturing the dura layer. The desired intracranial pressure may be measured by the pressure transducer, e.g., by measuring the pressure at the time of dura puncture. Alternatively, the desired intracranial pressure may be measured by some other pressure measuring mechanism prior to puncturing the dura. In another alternative, the intracranial pressure may be calculated, (e.g., based on patient's demographics such as age, weight, blood pressure, etc.) rather than measured.

In order to maintain a substantially constant intracranial pressure, fluid is added to the cranial cavity when a drop in pressure is detected by the pressure transducer, and fluid is removed from the cranial cavity when an increase in intracranial pressure is detected by the pressure transducer. Thus, when a pressure drop is detected, the plunger 532 is manually depressed in order to add fluid to the cranial cavity, and when a pressure increase is detected, the plunger 532 is manually pulled in the proximal direction in order to remove fluid from the cranial cavity. The user of the device 500 may be cognizant of when to operate the plunger 532 by, e.g., monitoring a pressure gauge coupled to the pressure transducer, the sounding of an alarm coupled to the pressure transducer, or the like.

Fluid may flow into and out of the cranial cavity through an opening in the dura layer. In this embodiment, the dura has been excised in some way. For example, when the stimulation lead 100 is disposed through the dura layer, the dura layer does not form a tight seal around the diameter of the lead 100 and, thus, fluid may flow through the space between the dura layer and the lead 100. Alternatively, the dura may be excised in some other manner to provide a fluid path between the syringe fluid chamber 528 and the cranial cavity. In another alternative, the device 500 may be attached to the burr hole after the dura layer has been punctured, and the syringe 520 may then be used to normalize the intracranial pressure.

During use, the suction cup ring 502 is attached to tissue adjacent to a burr hole. Similar to the suction cup ring 202 of the sealing device 200 described above, the suction cup ring 502 may be attached above the burr hole to the portion of the skull bone that surrounds the top of the burr hole (similar to FIG. 4), or may be positioned within the burr hole and attached directly to the dura layer exposed at the bottom of the burr hole (similar to FIG. 3A). The syringe 520 may be attached to the suction cup ring 502 either before or after the suction cup ring 502 is attached to the tissue.

After the sealing device 500 is correctly positioned, the stimulation lead 100 may be introduced through the central channel 526 in the syringe 520 and through the membrane 504 disposed at the distal end of the central channel 526, as depicted in FIGS. 5C and 5D. After puncturing the membrane 504, the lead 100 punctures the dura layer and is implanted into the brain tissue. Substantially similar to the inner membrane 204 of sealing device 200, the inner membrane 504 is configured for allowing the stimulation lead 100 to pass therethrough while forming a tight seal around the diameter of the stimulation lead 100.

While the lead 100 is disposed through the dura layer, the sealing device 500 is operated to maintain a substantially fixed intracranial pressure during the stimulation lead implantation procedure by actively maintaining a substantially fixed volume of CSF within the cranial cavity. That is, the plunger 532 is manually operated to add fluid to, or remove fluid from, the cranial cavity in response to a change in intracranial pressure, as discussed above. Thus, the sealing device 500 is a two piece system for actively and manually maintaining the substantially fixed intracranial pressure and preventing brain shift during implantation of the stimulation lead 100.

Figure 6A:
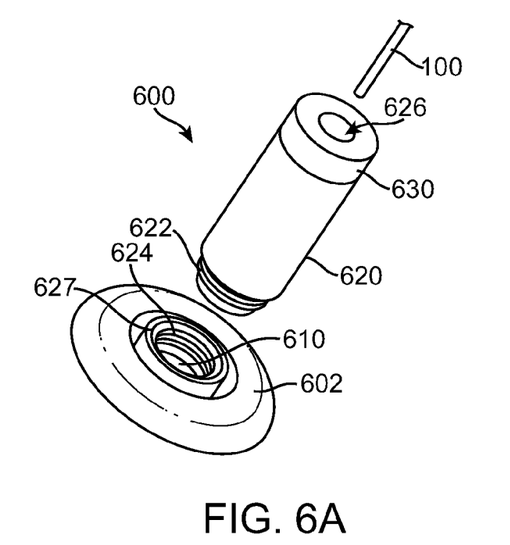
FIG. 6A is a partially exploded perspective view of a burr hole sealing device constructed in accordance with yet another embodiment of the present inventions.
Figure 6B:
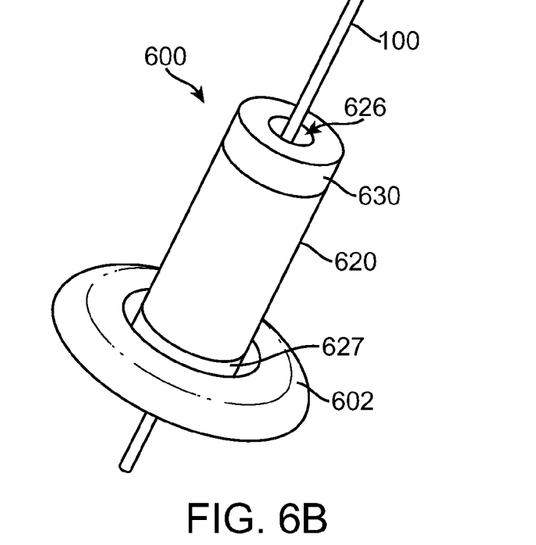
FIGS. 6B and 6C are perspective views of the burr hole sealing device depicted in FIG. 6A.
Figure 6C:
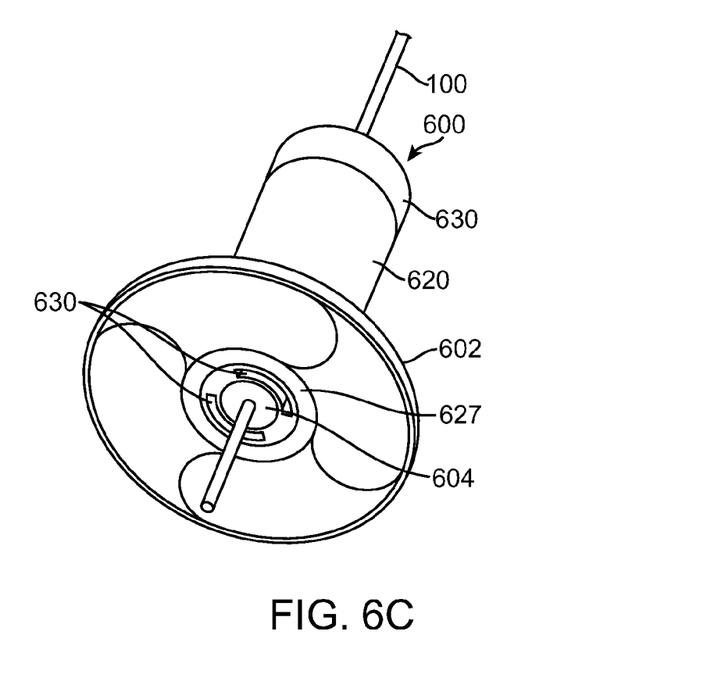

In yet another embodiment of a burr hole sealing device, the plunger may be coupled to a feedback controller for actively and automatically adjusting the fluid volume within the cranial cavity, thereby maintaining the substantially constant intracranial pressure. For example, the burr hole sealing device 600 shown in FIGS. 6A-6C is similar to the burr hole sealing device 500 described above, except that the syringe body 620 is coupled to a feedback controller, shown schematically as 630. The controller 630 includes a pressure transducer (not shown) coupled to a pressure regulator (not shown), which sends signals to an actuator (i.e., a motor or the like, not shown) that is coupled to a syringe plunger (not shown) and/or a pump (not shown). The feedback controller 630 is thus configured for detecting a change in intracranial pressure and for automatically operating the plunger and/or the pump to add fluid to, or remove fluid from, the cranial cavity.

Similar to the burr hole sealing device 500 shown in FIGS. 5A-5E, the burr hole sealing device 600 includes an attachment mechanism, such as a suction cup ring 602, for facilitating attachment of the device 600 to tissue adjacent to a burr hole. In addition, similar to the device 500, the device 600 includes an aperture 610 in the ring 602, a central passageway 626 in the syringe 620 through which the lead 100 may be disposed during the stimulation lead implantation procedure, a fluid chamber (not shown) surrounding the central passageway 626, a membrane 604 disposed on the distal end of the central passageway 626, a fluid opening 630 disposed on the distal end of the fluid chamber and at least partially surrounding the membrane 604, a threaded collar 627, and cooperating threads 622, 624 for attaching the syringe 620 to the suction cup ring 602. The device 600 may be placed on or within the burr hole before or after the dura layer has been punctured, similar to the device 500 discussed above.

In the illustrated embodiment, the inner membrane 604 may be mechanically connected to the pressure transducer that is part of the controller 630. The pressure transducer is configured to measure the deflection or the capacitance of the membrane 604. The measurement is used by the controller 630 to calculate the intracranial pressure. If a change in pressure is detected, the feedback controller 630 is configured to automatically activate the plunger and/or the pump for adding fluid to, or removing fluid from, the cranial cavity.

Additionally or alternatively, a valve (not shown) may be coupled to the syringe 620. The feedback controller 630 may be configured to automatically open and close the valve. In one embodiment, the syringe 620 may include a manually operated plunger, such that fluid is allowed to flow into the cranial cavity only when the valve is automatically opened and the manually operated plunger is depressed. Such an arrangement may also include an alarm for alerting the user to operate the plunger. Alternatively, the syringe may include an automated plunger and/or pump coupled to the valve and the feedback controller 630.

Figure 7:
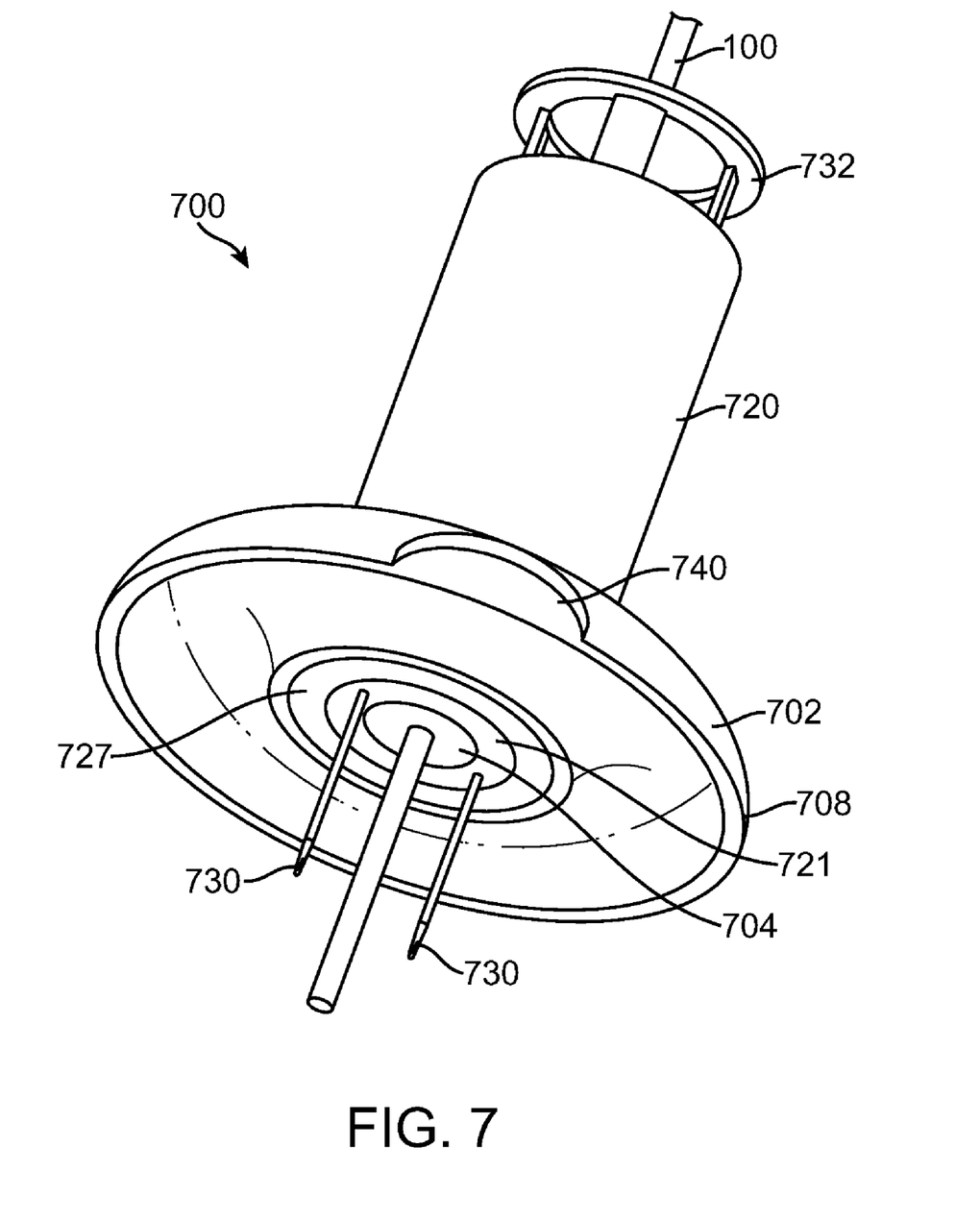
FIG. 7 is a perspective view of a burr hole sealing device constructed in accordance with still another embodiment of the present inventions.

Referring now to FIG. 7, another embodiment of a burr hole sealing device 700 will be described. The burr hole sealing device 700 is similar to the burr hole sealing device 500 described above, except that, rather than having fluid openings 530 at the distal end of the fluid chamber 528, the syringe 720 includes needles 730 coupled to the distal end 721 of the syringe body for facilitating fluid flow directly between the syringe fluid chamber (not shown) and the cranial cavity. It should be well understood that, although the burr hole sealing device 700 is depicted with a manually operated syringe 732, the device 700 may alternatively include any of the feedback control arrangements discussed above for automatically maintaining the substantially fixed intracranial pressure.

Similar to previous embodiments, the burr hole sealing device 700 includes a suction cup ring 702 for attaching the device 700 to a burr hole. A tab 740 coupled to the outer diameter 708 of the suction cup ring 702 facilitates easy removal of the sealing device 700. That is, the sealing device 700 can be easily detached from the tissue surface by pulling the tab 740, thereby releasing the vacuum seal between the suction cup ring 702 and the tissue surface. It should be well understood that the tab 740 could be incorporated into the other embodiments discussed herein as well. The device 700 also includes a central passageway (not shown) in the syringe 720 through which the stimulation lead 100 is disposed during the stimulation lead implantation procedure, a fluid chamber (not shown) surrounding the central passageway, a membrane 704 disposed on the distal end of the central passageway, a threaded collar 727, and cooperating threads (not shown), all of which operate in a substantially similar manner to that described in the previous embodiments. The device 700 may be placed on or within the burr hole before or after the dura layer has been punctured, similar to the devices 500 and 600 discussed above.

Figure 8A:
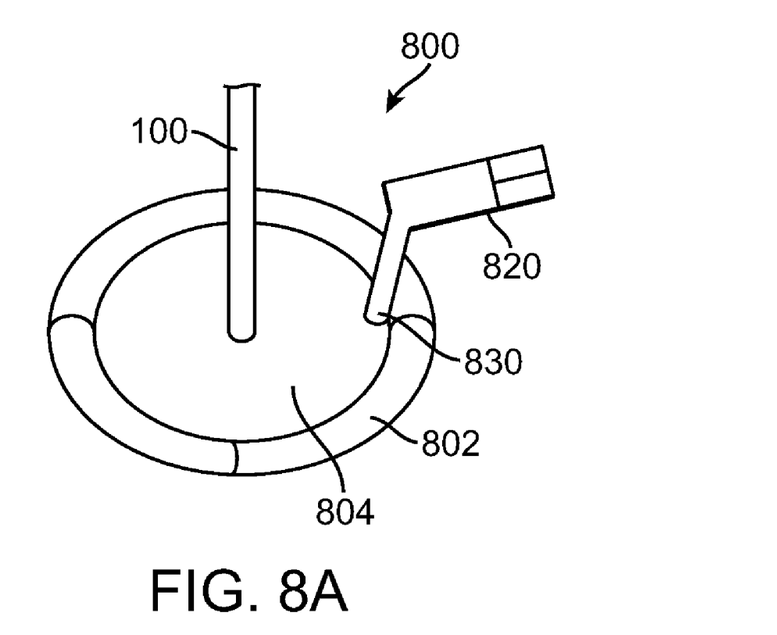
FIGS. 8A and 8B are perspective and bottom views, respectively, of a burr hole sealing device constructed in accordance with yet another embodiment of the present inventions.
Figure 8B:
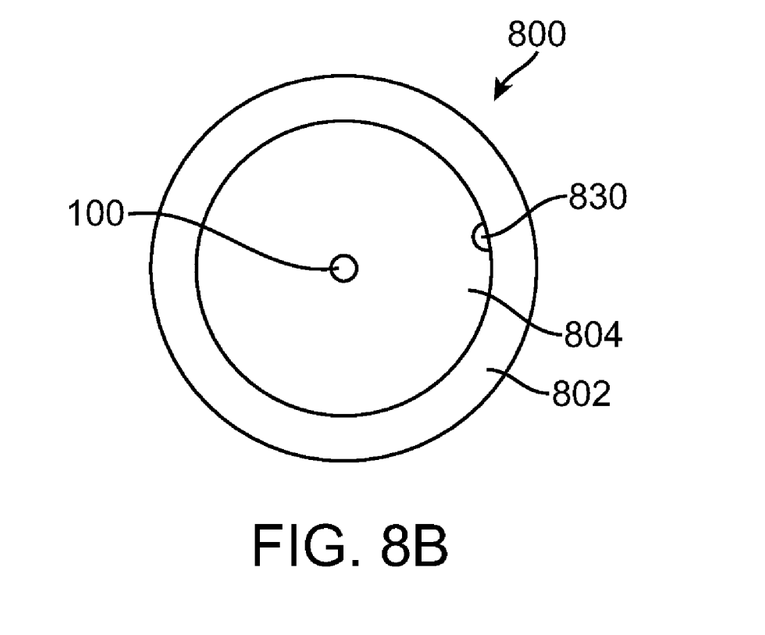

Referring now to FIGS. 8A and 8B, yet another embodiment of a burr hole sealing device 800 will be described. In order to accommodate bulky stereotactic equipment that may be positioned above the burr hole, the burr hole sealing device 800 includes a syringe 820 that is configured for being positioned adjacent to an outer edge of the inner membrane 804 such that the syringe 820 may still access the burr hole even when working space is quite limited by the stereotactic targeting apparatus. Notably, in this embodiment, the stimulation lead 100 does not pass through a central passageway in the syringe 820. Rather, the syringe needle 830 punctures the membrane 804 at a location that is adjacent to the location where the stimulation lead 100 passes through the membrane 804. The membrane 804 is configured for allowing the stimulation lead 100 and the syringe needle 830 to pass therethrough while maintaining a tight seal around the diameters of the syringe needle 830 and the stimulation lead 100. Similar to previous embodiments, the device 800 also includes a suction cup ring 802 for attaching the device 800 to tissue adjacent to the burr hole. The device 800 may be placed on or within the burr hole before or after the dura layer has been punctured, similar to the devices 500, 600, and 700 discussed above.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method for performing a medical procedure on a patient, comprising:
    attaching a burr hole sealing device adjacent to a cranial burr hole that exposes a dura layer, wherein the burr hole sealing device includes a syringe and an aperture disposed over the exposed dura layer;
    introducing an elongated medical device through the aperture of the sealing device, through the burr hole, through the dura layer, and into the brain tissue of the patient; and
    allowing the sealing device to maintain a substantially fixed intracranial pressure while the medical device is disposed through the dura layer, wherein maintaining the substantially fixed intracranial pressure comprises at least one of adding fluid and removing fluid through the syringe.

2. The method of claim 1, wherein introducing the elongated medical device comprises passing the elongated medical device through a central channel in the syringe, and wherein adding and removing the fluid is performed through a fluid chamber surrounding the central channel.

3. The method of claim 1, wherein the burr hole sealing device comprises an inner membrane, and the method further comprises puncturing the inner membrane with the syringe.

4. A method for performing a medical procedure on a patient, comprising:
    attaching a burr hole sealing device adjacent to a cranial burr hole that exposes a dura layer, wherein the burr hole sealing device comprises a suction cup ring surrounding an inner membrane, and an aperture disposed over the exposed dura layer;
    introducing an elongated medical device through the aperture of the sealing device, through the burr hole, through the inner membrane, through the dura layer, and into the brain tissue of the patient; and
    allowing the sealing device to maintain a substantially fixed intracranial pressure while the medical device is disposed through the dura layer.

5. The method of claim 4, wherein attaching the burr hole sealing device adjacent to the burr hole comprises vacuum sealing the suction cup ring to a surface adjacent to the burr hole and attaching the inner membrane to the ring.

6. The method of claim 4, wherein attaching the burr hole sealing device adjacent to the burr hole comprises vacuum sealing the suction cup ring to a top surface of a skull bone that surrounds the burr hole.

7. The method of claim 4, wherein attaching the burr hole sealing device adjacent to the burr hole comprises vacuum sealing the suction cup ring to the dura layer.

8. A burr hole sealing system, comprising:
    a sealing mechanism configured to be attached adjacent a cranial burr hole, to allow an elongated medical device to be disposed through a dura layer and into a cranial cavity, and to hinder leakage of cerebrospinal fluid from the cranial cavity while the elongated medical device is disposed through the dura layer; and
    a syringe attached to the sealing mechanism and configured for maintaining a substantially fixed intracranial pressure within the cranial cavity while the elongated medical device is disposed through the dura layer, wherein the syringe comprises a central passage, a fluid chamber surrounding the central passage, and a membrane on a distal end of the central passage, wherein the central passage and the membrane are configured for allowing the elongated medical device to pass therethrough.

9. The system of claim 8, wherein the syringe comprises a manually operated plunger.

10. A burr hole sealing system, comprising:

a sealing mechanism configured to be attached adjacent a cranial burr hole, to allow an elongated medical device to be disposed through a dura layer and into a cranial cavity, and to hinder leakage of cerebrospinal fluid from the cranial cavity while the elongated medical device is disposed through the dura layer, wherein the sealing mechanism comprises an inner membrane configured for forming a seal around a diameter of the elongated medical device while the elongated medical device is disposed through the dura layer, and wherein the sealing mechanism includes a suction cup ring comprising an aperture, and the inner membrane is disposed within the aperture of the suction cup ring; and a syringe attached to the sealing mechanism and configured for maintaining a substantially fixed intracranial pressure within the cranial cavity while the elongated medical device is disposed through the dura layer.

11. A burr hole sealing system, comprising:

a sealing mechanism configured to be attached adjacent a cranial burr hole, to allow an elongated medical device to be disposed through a dura layer and into a cranial cavity, and to hinder leakage of cerebrospinal fluid from the cranial cavity while the elongated medical device is disposed through the dura layer;

a syringe attached to the sealing mechanism and configured for maintaining a substantially fixed intracranial pressure within the cranial cavity while the elongated medical device is disposed through the dura layer, wherein the syringe comprises a plunger;

a pressure transducer configured for monitoring the intracranial pressure; and a pressure regulator in communication with the pressure transducer, wherein the pressure regulator is configured for automatically operating the plunger in response to a change in pressure detected by the pressure transducer.

* * * * *